(12) United States Patent
Vacanti et al.

(10) Patent No.: US 7,319,035 B2
(45) Date of Patent: Jan. 15, 2008

(54) BIOLOGICAL SCAFFOLDING MATERIAL

(75) Inventors: Martin P. Vacanti, Westborough, MA (US); Charles A. Vacanti, Uxbridge, MA (US)

(73) Assignee: VBI Technologies, L.L.C., Houston, TX (US)

( * ) Notice: Subject to any disclaimer, the term of this patent is extended or adjusted under 35 U.S.C. 154(b) by 383 days.

(21) Appl. No.: 10/688,305

(22) Filed: Oct. 17, 2003

(65) Prior Publication Data

US 2004/0137613 A1 Jul. 15, 2004

Related U.S. Application Data

(60) Provisional application No. 60/419,682, filed on Oct. 17, 2002.

(51) Int. Cl.
*C12N 5/08* (2006.01)
*A61K 9/00* (2006.01)

(52) U.S. Cl. .................. 435/366; 435/325; 424/400; 424/422; 424/93.1

(58) Field of Classification Search .......... 424/400, 424/422, 93.1; 435/395, 366
See application file for complete search history.

(56) References Cited

U.S. PATENT DOCUMENTS 5,041,138 A   8/1991   Vacanti et al.
5,716,404 A * 2/1998   Vacanti et al. .............. 623/8
5,855,610 A   1/1999   Vacanti et al.
6,026,744 A   2/2000   Miyata

OTHER PUBLICATIONS

Alho et al., "Assessment of malignancy of cartilage tumors using flow cytometry. A preliminary report," *J Bone Joint Surg Am.* 65-A(6):779-85 (1983).
Bonassar et al., "Tissue engineering: the first decade and beyond," *J Cell Biochem S30/31*:297-303 (1998).
Crissman et al., "Rapid, one step staining procedures for analysis of cellular DNA and protein by single and dual laser flow cytometry," *Cytometry* 3(2):84-90 (1982).
Kamil et al., "Tissue-Engineered Human Auricular Cartilage Demonstrates Euploidy by Flow Cytometry," *Tissue Engineering* 8:85-92 (2002).
Kreicbergs et al., "Prognostic factors in chondrosarcoma: a comparative study of cellular DNA content and clinicopathologic features," *Cancer* 50(3):577-83 (1982).
Vacanti et al., "Identification and initial characterization of spore-like cells in adult mammals", *J Cell Biochem* 80(3):455-60 (2001).
Yang et al., "The Design of Scaffolds for Use in Tissue Engineering", *Tissue Engineering* 7:679-689 (2001).

* cited by examiner

*Primary Examiner*—Ruth A Davis
(74) *Attorney, Agent, or Firm*—Pabst Patent Group LLP

(57) ABSTRACT

The invention provides methods of generating a natural, living biological matrix that can serve as, or form a part of, a natural biological scaffold. The matrix is generated by incubating together biological cells and cellular debris. Any naturally occurring cell can be a biological cell included in the matrix. The invention also provides methods of treating a patient by implanting the matrix or scaffolding into a tissue of the patient, thereby augmenting the existing tissue.

32 Claims, 13 Drawing Sheets

BIOLOGICAL SCAFFOLDING MATERIAL

RELATED APPLICATIONS

This application claims the benefit of U.S. Provisional Application No. 60/419,682, filed on Oct. 17, 2002, the subject matter of which is incorporated herein by reference in its entirety.

TECHNICAL FIELD

This invention relates to compositions and methods for generating a biological scaffold that can be used, for example, in tissue engineering.

BACKGROUND

The field of tissue engineering explores the ways in which cell culture technology can be combined with polymer technology to generate new tissues of predesigned shape and volume (see *Principles of Tissue Engineering*, Second Edition, Lanza et al., Eds., Academic Press, 2000). The field is largely grounded in the idea that biological tissues can be generated or repaired through the application and control of cells, synthetic materials, and chemo-attractive proteins (reviewed in Bonassar and Vacanti, *J. of Cell. Biochem.* Supp., 30/31: 297-303, 1998). Tissue engineering technology offers the promise of tissue regeneration and replacement following trauma or a variety of diseases or birth defects. It can also be used in the context of cosmetic procedures.

Both autologous and heterologous tissue or cells can be made in tissue engineering techniques. The use of autologous tissue in tissue engineering provides advantages in that it helps to reduce the risk that the engineered tissues will provoke an immune response. In some instances, when creating an autologous implant, donor tissue is harvested and dissociated into individual cells, and the cells are attached and cultured on a substrate that is implanted at the desired site of the functioning tissue. Many isolated cell types can be expanded in vitro using cell culture techniques. However, primary organ cells, which are often in demand in tissue engineering, are generally believed to be anchorage dependent and to require specific environments, often including the presence of a supporting material, or scaffold, to act as a template for growth. Current tissue engineering technology provides an artificial extracellular matrix for cell culture. Since successful cell transplantation therapy depends on the development of suitable substrates for both in vitro and in vivo tissue culture, the development of an extracellular matrix that contains natural materials and that is suitable for implantation would have more of the characteristics of the endogenous tissue. This is an ongoing challenge in the field of tissue engineering (see Yang et al., *Tissue Engineering* 7:679-689, 2001).

SUMMARY

The present invention is based, in part, on the discovery that biological cells and cellular debris (e.g., cellular remnants (e.g., nuclei, membrane fragments, or organelles) and components (e.g., proteins, peptides, lipids, nucleic acids, and carbohydrates)) can be cultured together (all together or in various combinations or fractions) as a heterogeneous biological mixture, and that this mixture can be extracted from the culture medium to form a natural, living biological matrix. This matrix can itself serve as, or form a part of, a natural biological scaffold. The biological cells that can be included in the matrix include any cells, whether differentiated, partially differentiated, or undifferentiated (e.g., stem cells or progenitor cells, which are discussed further below), and can be derived from any tissue type (e.g., ectoderm, endoderm, or mesoderm).

Whole cells, including those that can divide and/or differentiate into one, two, three, or more mature cell types, add developmental potential to the matrix; when such cells give rise to a differentiated cell, or to a variety of different cell types, they augment the injured or defective tissue to which the matrix or scaffold is applied. The augmentation can be physical (for example, the cells can provide mass (e.g., muscle or bone (or other connective tissue) mass) or proteins (e.g., the cells can provide one or more molecules necessary for tissue function or growth, such as growth factors, cytokines, neurotransmitters, or hormones).

The invention also provides methods of treating patients by implanting the matrix or scaffolding into a tissue of the patient, such as the heart, pancreas, lung, kidney, or liver; into or around a joint, in or around the head or neck, into the spinal cord or onto an area of the skin (implantation "into" or "onto" a tissue means contacting the implanted material with a tissue; the matrix or scaffold can be wholly implanted within a tissue; partially implanted, or simply placed adjacent to (or upon or between) the tissue).

In these methods, matrix implanted into a joint or other region that contains cartilage is induced to produce proteoglycans. Matrix implanted into lung tissue is induced to synthesize collagen and/or an elastic fiber. Matrix implanted into tissues of the central nervous system (CNS) is induced to synthesize laminin (which can guide the development of axons or any processes extending from neurons). Matrix implanted into muscle (cardiac, skeletal, or smooth), is induced to differentiate into cardiac, skeletal, or smooth myocytes. Matrix implanted into the pancreas is induced to synthesize insulin, glucagon, or another pancreatic hormone.

Matrix that contains or develops to contain or produce cells or cell products, can augment the patient's existing tissue, whether that tissue is damaged or not. The implantation sites described above are merely examples of the tissues that can be augmented; the new matrix and the biological scaffold it forms can be used in any circumstance where conventional tissue engineering techniques would be employed or considered.

The invention also features methods that can be used to isolate biological material that can be incorporated into the matrix. The "starting material" can be whole blood, a fraction of blood, or tissue that arises from any of the three germ layers (the mesoderm, endoderm, or ectoderm), e.g., from an organ such as the brain (or spinal cord), liver, lung, or skin. Methods for culturing the matrix; and, as noted above, methods for treating a patient (e.g., a human patient with some type of tissue injury or defect) with the matrix are also disclosed. The methods for treating patients include one or more steps in which a cultured matrix is implanted into a patient, e.g., into a tissue that is in some way defective. The means for implanting the matrix can vary and are described further below. While the methods are not limited to those in which any particular biological event occurs, the matrix (or components of the matrix) can respond to environmental cues that cause it to take on at least one of the characteristics of the surrounding tissue.

Generally, an implanted matrix will produce at least one of the following: collagen (e.g., any of collagens 1-9), glycoprotein, fibronectin, laminin, thrombospondin, elastin, fibrillin, mucopolysaccharides, glycolipids, heparin sulfate, chondroitin sulfate, keratin sulfate, glycosaminoglycans, or hyaluronic acid.

As noted above, the "starting material" for the biological matrix or scaffold can be a sample of blood obtained from a subject, such as a human patient. The blood can be frozen after it is obtained (at any temperature at or below freezing, including down to at least −70° C.), and the blood can be stored in this state for an indefinite period of time (hours, a day, several days, a week, weeks, months, or years). Alternatively, the biological matrix or scaffold can be generated from a sample of cartilage (e.g., auricular cartilage) obtained from a subject, such as a human patient.

While the density or porosity of the matrix can vary greatly at the time of administration to a patient, it cannot be so dense that it totally prohibits the ingress or egress of cells, cellular processes (e.g., neurites), and nutrients. The matrix (either on its surface, within its pores or channels, or both) can possess one or more of the characteristics exhibited by extracellular matrix (e.g., it can facilitate dynamic cell attachment).

In certain embodiments, a substance can be added to the cell culture to supplement the matrix or a property of the matrix. For example, a hydrogel or an adhesive can be added to provide shape, structure, or support to the matrix. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions, cross-linking, or similar means. The hydrogels used in conjunction with the matrices described herein can solidify so rapidly that the majority of the cells or cellular components within the matrix are retained or trapped. This retention enhances new cell growth at the application site. The hydrogels are also biocompatible (i.e., they are not toxic to cells). The "hydrogel-cell composition" referred to herein includes a hydrogel and a cellular matrix of the invention. Furthermore, the sterility of a matrix or scaffold can be enhanced by heating or freezing it or by the addition of antibiotic agents.

The matrix can also be supplemented with additional cells. For example, one can "seed" the cultured matrix (or co-culture it) with undifferentiated cells (e.g., spore-like cells or other precursor cells). These cells can also be autologous, and they can also originate either from a bodily fluid (e.g., blood or cerebrospinal fluid) or a tissue, organ, or organ system (regardless of whether that tissue or organ derived from ectoderm, mesoderm, or endoderm). The cells can produce a scaffold that resembles collagen, basement membrane, or laminin.

The matrix can include so-called "spore-like" progenitor cells, also called "spore-like cells" or "spore-like bodies." These spore-like cells can vary greatly in their size. For example, they can have a very small diameter (less than one to about three, five, or seven microns), or they can be mid- to large-sized (having a diameter of about 10, 12, 15, or 20 microns). Spore-like cells are most typically less than 5 microns in diameter. Spore-like cells can also be more tolerant of extreme conditions (such as oxygen-deprivation) than can be differentiated cells. Electron micrographs and histological stains for nucleic acids indicate that a large portion (e.g., at least about 50% and up to 90% or more) of the volume of a spore-like cell is comprised of nucleic acids. The outer edges of the spore-like cells are surrounded by mucopolysaccharides and glycolipids. Spore-like cells can be obtained from various tissues, organs, and bodily fluids, as can stem cells or progenitor cells. For example, these cells can be isolated from bodily fluids (e.g., blood or cerebrospinal fluid) of a post-natal animal (e.g., a mammal) or from solid organs such as the heart (or other muscle types, such as smooth or skeletal muscle), intestine, bladder, kidney, liver, lung, adrenal gland, skin, retina, or pancreas.

Also described herein are methods for increasing the amount of material in a biological scaffold or matrix by reculturing the material (cells or cellular debris) present in the culture medium that is removed (and normally discarded) from the tissue culture flask when the cultures are passaged. The "cellular debris" present in the matrix and scaffold includes cell fragments, which includes membrane fragments, lipids, and proteins released from disrupted cells.

Given that the procedures described herein generate a matrix or scaffold that consists largely (or even wholly) of natural biological materials, the result is a dynamic, responsive, living matrix (and therefore distinct from the result obtained when conventional biodegradable materials are used in tissue engineering). Moreover, in the event the materials used are "self-derived," it is highly unlikely that the matrix will elicit an immune response (that can encourage degradation or rejection of the matrix) as a "foreign" body would, and it is highly unlikely that they will transmit a contagious disease. Regardless of whether or not the materials selected are autologous, they are easy to obtain. For example, a convenient source of material for the biological matrix is the blood. The methods described herein and the matrix or scaffold produced also help meet one of the most significant challenges in tissue engineering because they generate enough cells from a source tissue to create a new tissue for implantation. The methods of the present invention allow one to generate, for example, about 200 million cells from only about 300,000 (enough to generate a human ear from a punch biopsy) in a matter of weeks or months.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. The contents of all references, pending patent applications and published patents, cited throughout this application are hereby expressly incorporated by reference. In case of conflict, the present specification, including definitions, will control.

The details of one or more embodiments of the invention are set forth in the accompanying drawings and the description below. Other features, objects, and advantages of the invention will be apparent from the description and drawings, and from the claims.

The image shows fragments of lobular cartilaginous tissue. The lacunae of the lobular tissue are round to oval, and in many cases have not formed discreet boundaries. The lacunae contain single cells with rounded nuclei. The specimen is highly cellular and somewhat irregular in architecture. There are some cellular areas of fibrous tissue with a sprinkling of chronic inflammation. The matrix is lightly basophilic in the cartilaginous areas and eosinophilic in the more fibrous areas. Additional sections revealed more discreet cartilage formation with more regularly spaced and shaped lacunae containing single cells.

Figure 3:
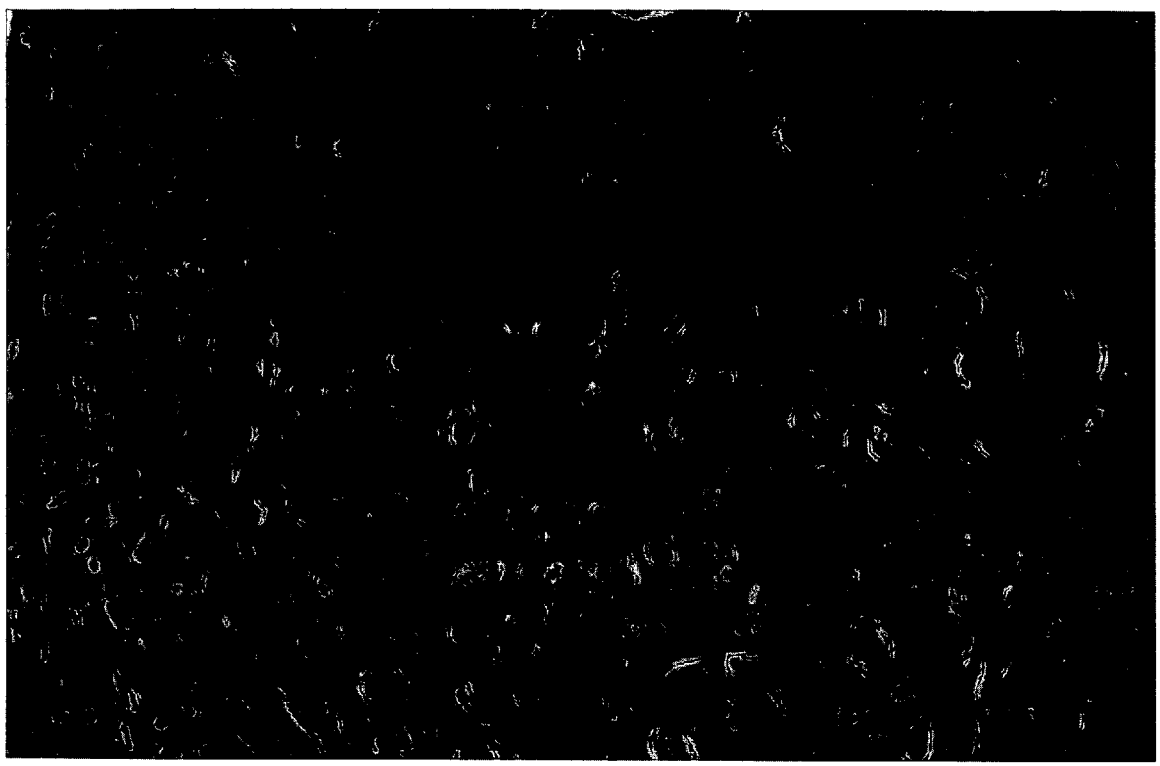

FIG. 3 is a photomicrograph of a floating cell population cultured from human auricular cartilage (see Example 1). This image shows fragments of myxoid tissue with a lightly eosinophilic matrix with focal areas of more evenly spaced cells and a hint of lacunae formations suggestive of immature cartilage. Other sections show essentially the same histology, but have more discreet areas of immature cartilage formation. These latter sections have a myxoid quality, a hint of lacunae formation, and a very slight basophilic tint in the center of the immature cartilage regions. Positive Safranin O staining on the same sections, also in the center of the immature cartilage regions, indicates proteoglycan production.

Figure 2:
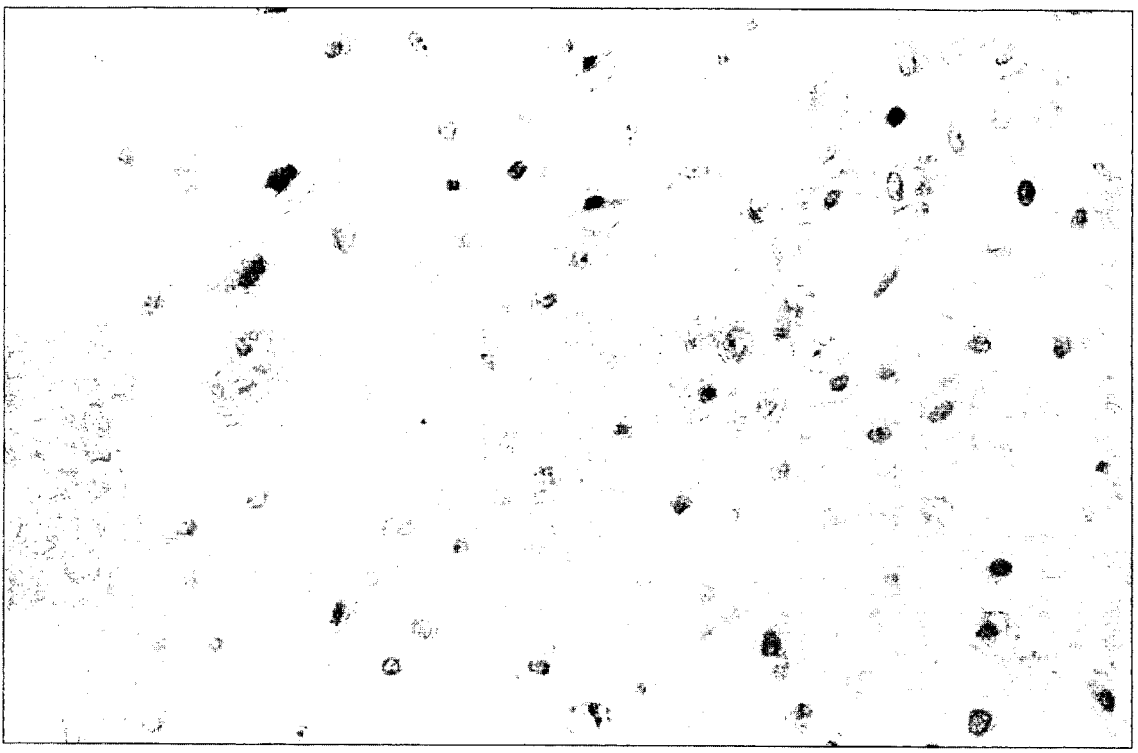
FIG. 2 is a photomicrograph of an attached cell population cultured from human auricular cartilage (see Example 1).
Figure 4:
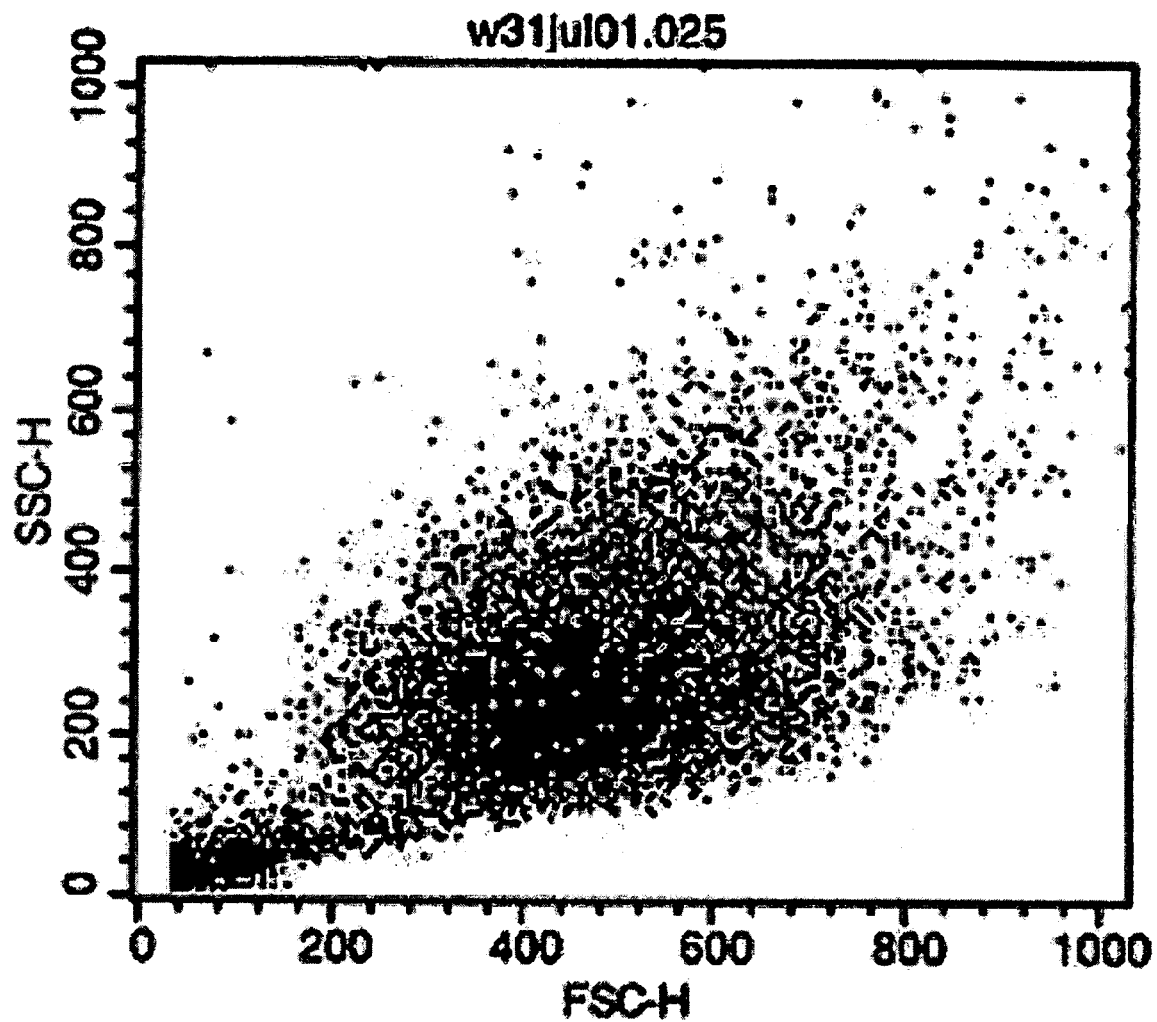

FIG. 4 is a flow cytometry scattergram of the attached cell population shown in FIG. 2. Side scatter (Y-axis) versus forward scatter (X-axis) are represented on the scattergram. A distinct population of intermediate forward scatter and low to moderate side scatter is indicative of a medium sized cell with low granularity, a characteristic of chondrocytes. The image also reveals evidence of apoptotic bodies in the areas proximal to the intersection of the X and Y-axis.

Figure 5:
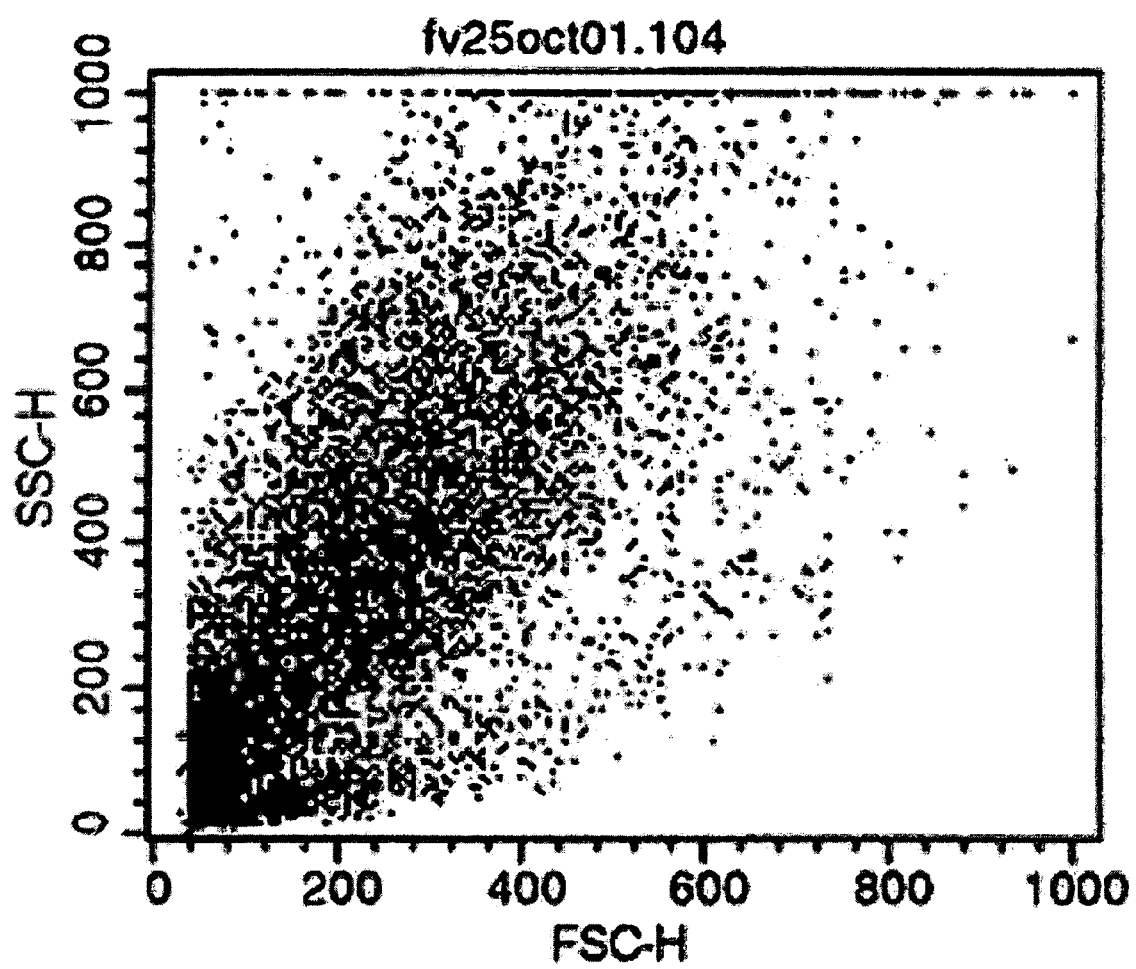

FIG. 5 is a flow cytometry scattergram of the floating cells shown in FIG. 3. The scattergram indicates that the floating cell population is comprised predominantly of a distinct population with moderate to high side scatter and low forward scatter indicating a small cell with granular characteristics. This is consistent with the physical characteristics of spore-like cells (Vacanti et al., *J. Cell. Biochem.* 80:455-60, 2001). A small percentage of cells overlaps in the coordinates found with chondrocytes. Thus, the scattergram reveals two distinct populations of floating cells.

Figure 6:
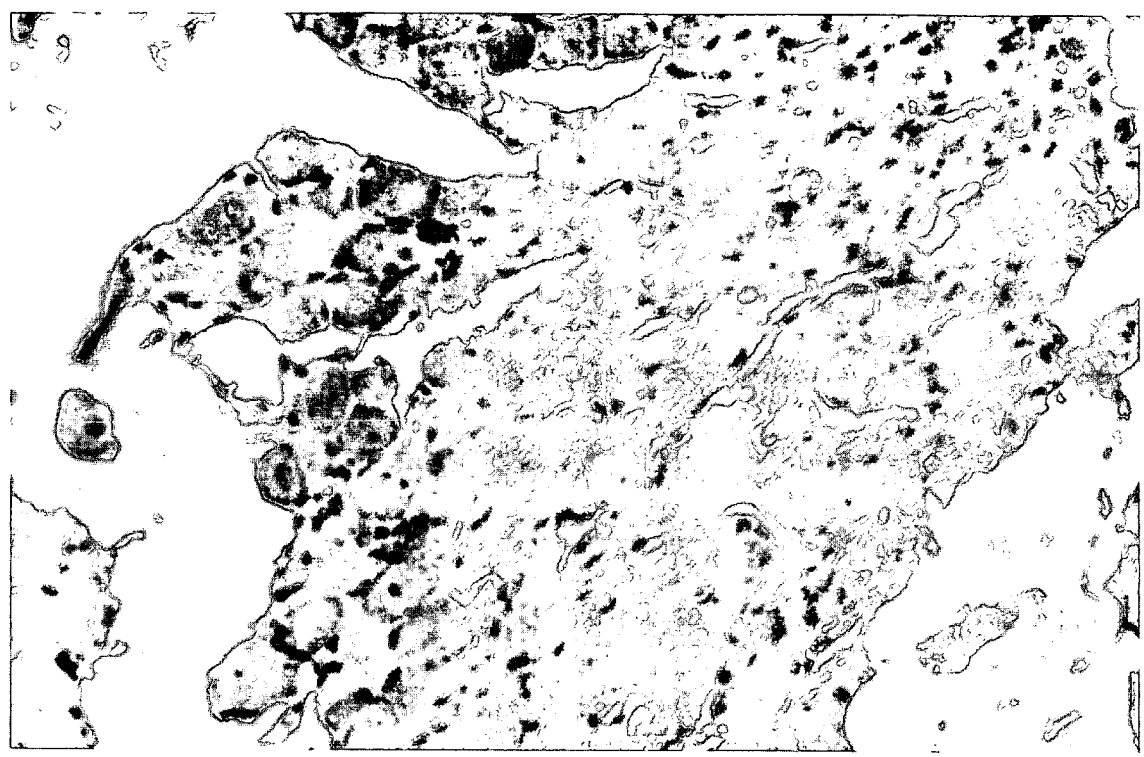

FIG. 6 is a photomicrograph of a histological section taken transversely and centered through the spinal cord of a rat sacrificed five weeks after implanting frozen rat blood-derived matrix into a complete T8-T9 surgically created gap (see Example 2). The attached construct is about 60% the diameter of normal cord (FIG. 7) (observed grossly). On the perimeter of the cord is fibrous scar and callous tissue (observed grossly). Neurons and capillaries are also visible in the attached construct.

Figure 7:
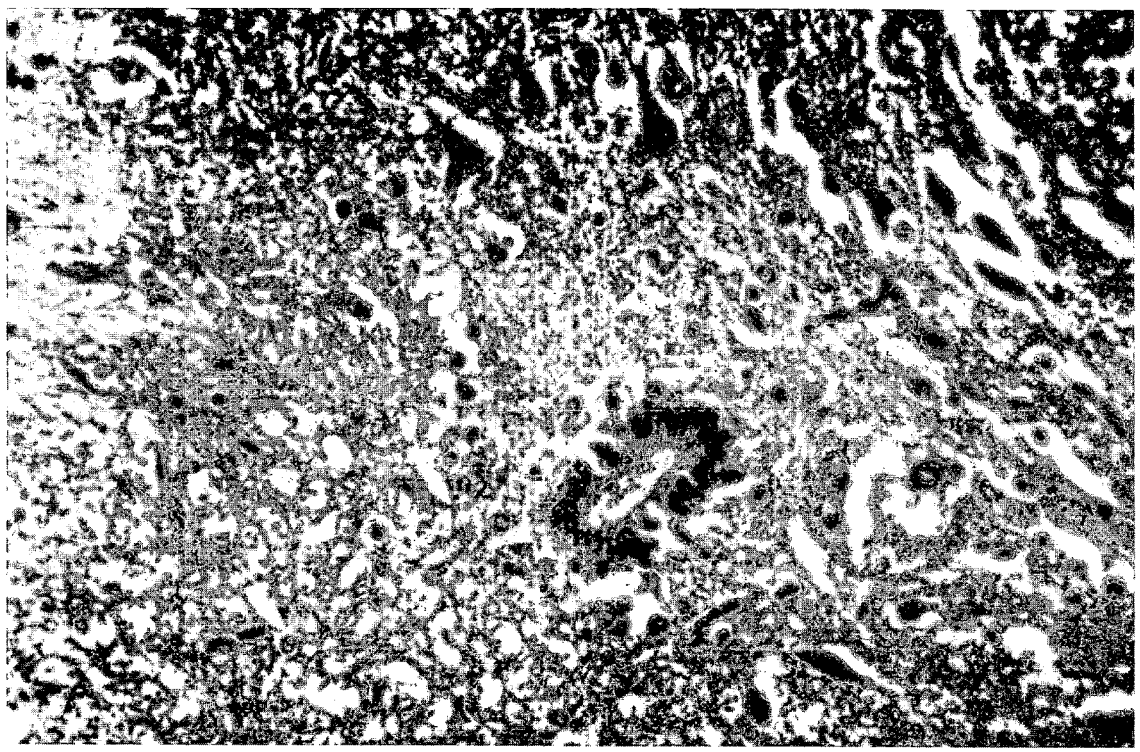

FIG. 7 is a photomicrograph of a histological section of native normal spinal cord.

Figure 8:
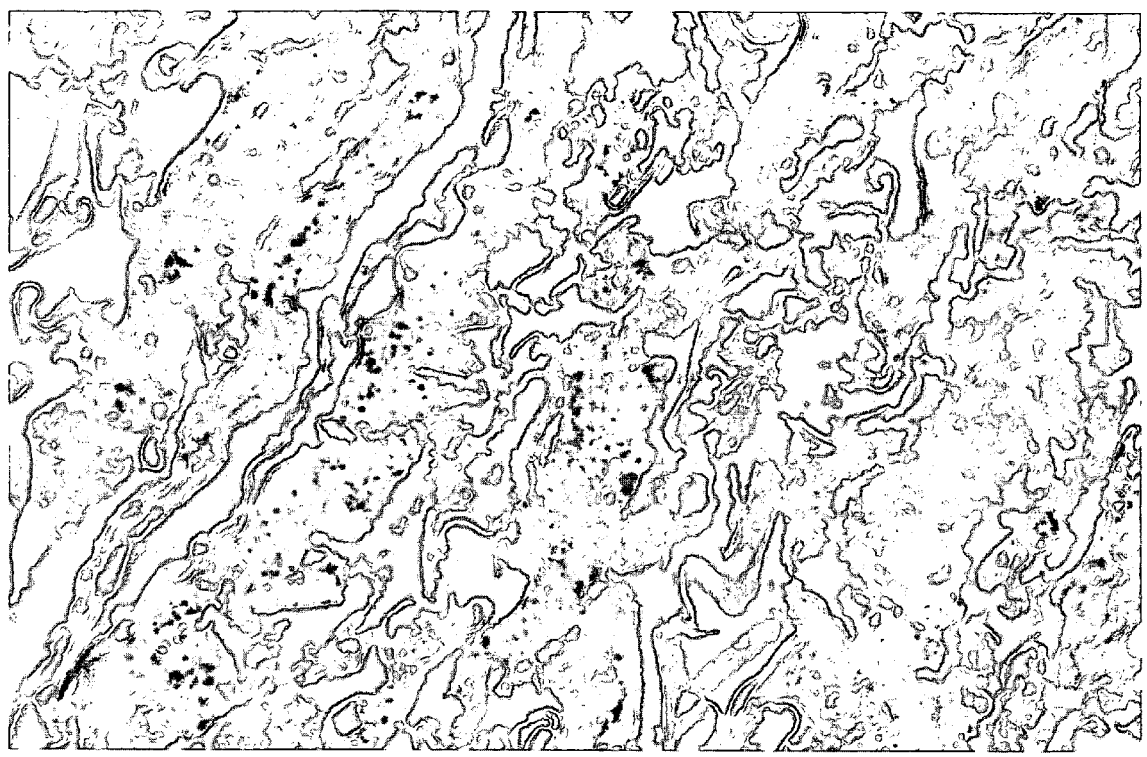

FIG. 8 is a photomicrograph of unprepared frozen anti-coagulated human blood following a periodic acid-Schiff stain (PAS). The darker areas indicate glycolipids and mucopolysaccharides.

Figure 9:
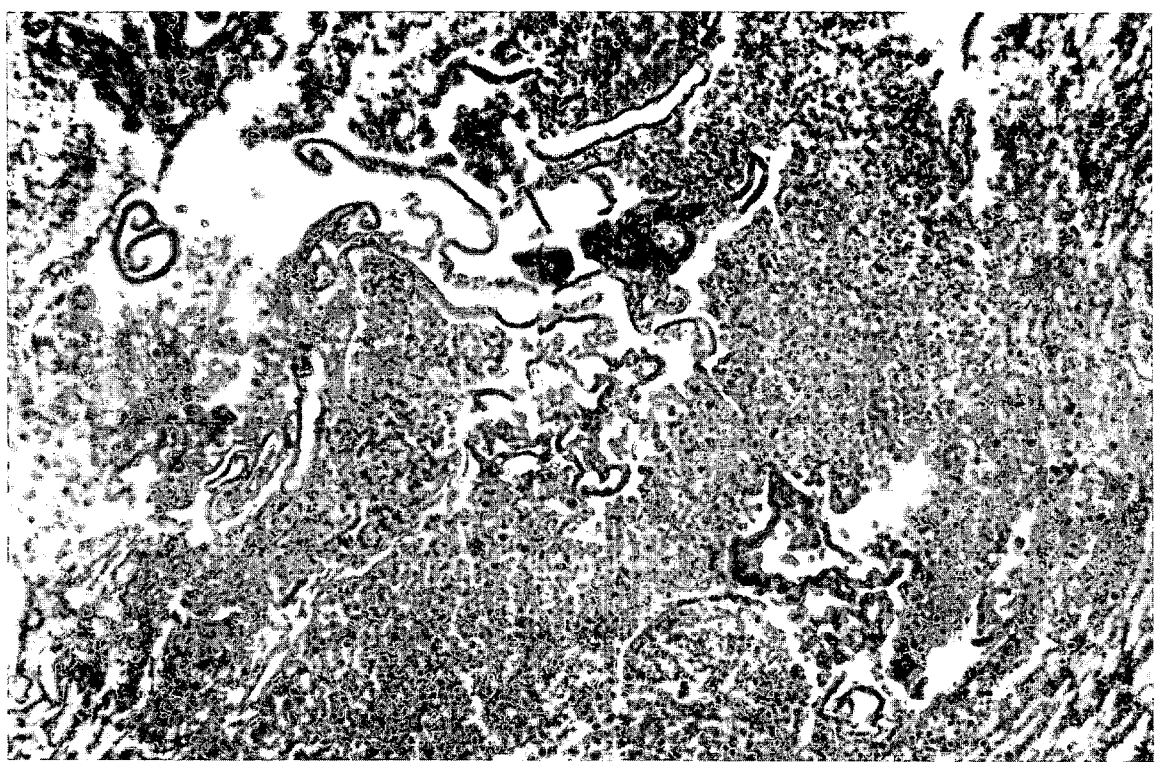

FIG. 9 is a photomicrograph of matrix prepared from frozen anticoagulated human blood stained with Safranin O. Positive staining indicates the presence of proteoglycans, the matrix material found in cartilage.

Figure 10:

FIG. 10 is a photomicrograph (a gross image) of floating matrix material prepared from frozen, anticoagulated human blood.

Figure 11:
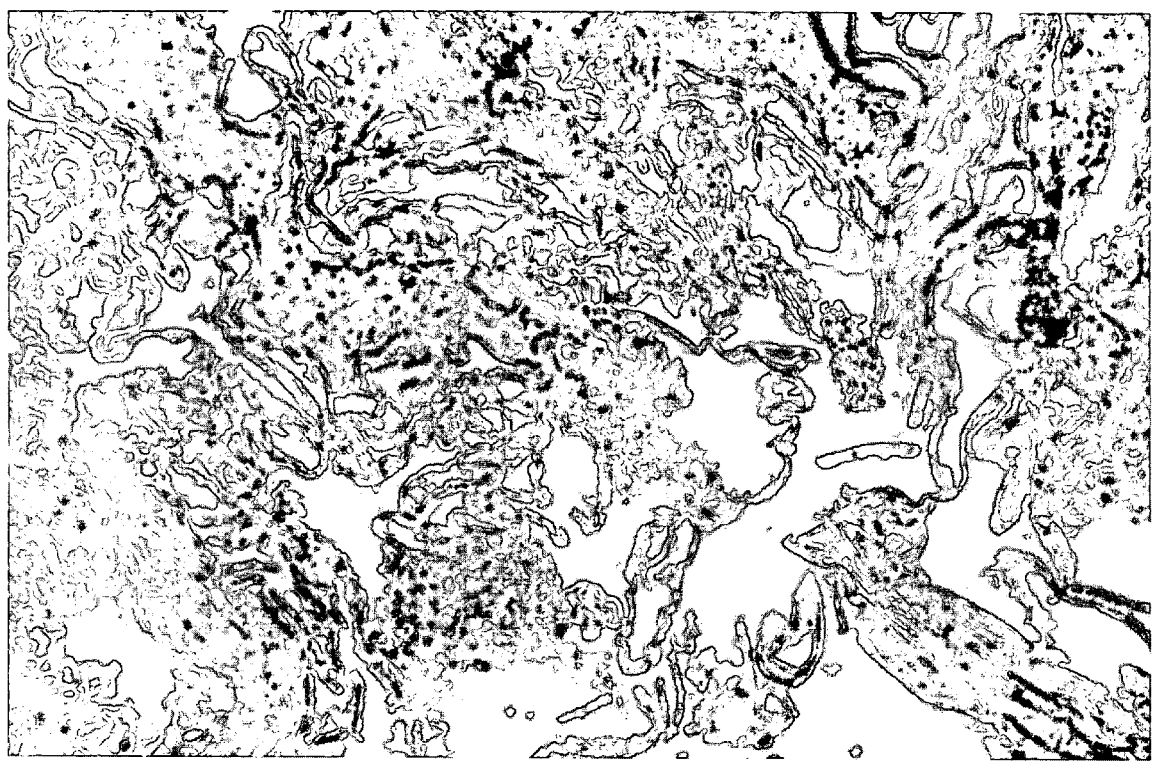

FIG. 11 is a photomicrograph of a matrix prepared from frozen, anticoagulated human blood that was stained with hematoxylin and eosin (H&E). The dark, curved lines are matrix material, and cellular debris is visible as the lighter material spread among the matrix.

Figure 12:
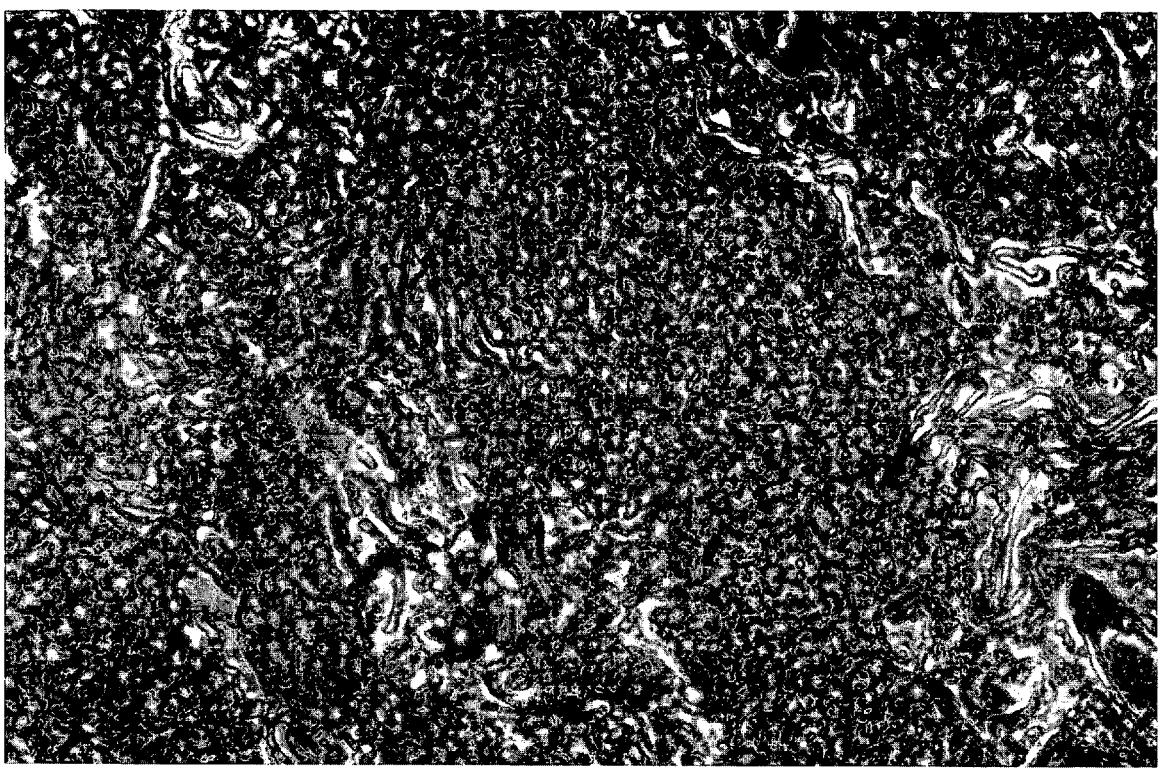

FIG. 12 is a photomicrograph of a cellular matrix (400×) at 19 days incubation. The matrix was prepared from frozen anticoagulated human blood. The small rounded structures are spore like-cells, embedded in the developing matrix (wavy material).

Figure 13:

FIG. 13 is a photomicrograph of matrix material prepared from frozen anticoagulated human blood and stained with trichrome. The dark areas (which appear dark green in the color version of this photomicrograph) indicate collagen production.

DETAILED DESCRIPTION

The present invention provides compositions and methods for generating a living matrix or scaffold that can respond to environmental cues and subsequently develop into, or augment the development of, a wide variety of different tissue types. Cells are included (e.g., enmeshed) in the matrix to produce a dynamic, responsive, living matrix. Generally, the methods are carried out using cells with cellular materials from a given tissue or bodily fluid (e.g., blood). Culturing the mixture allows for the formation of a cellular matrix that is multipotent and can be used for tissue engineering purposes. The scaffold is the matrix material itself, or the matrix with the addition of materials to give it support or shape. The term "scaffold" does not imply that there is any particular order or arrangement to the cells or other components of the scaffold.

Within the natural biological matrix, essential materials are actively synthesized. These materials can include one or more of: collagens 1-9, glycoproteins, and attachment material such as fibronectin, laminin, thrombospondin, elastin, and fibrillin. Various matrix substances such as mucopolysaccharides, glycolipids, heparin sulfate, chondroitin sulfate, keratin sulfate, glycosaminoglycans, and hyaluronic acid can also be produced. The dynamic, living matrix, with its cells, can guide the development of new tissue formation by generating the needed matrix material essential to tissue and organ development. For example, if placed in the CNS, the matrix will respond by making the essential CNS guiding material (e.g., laminin), which will allow neurons to attach and also guide their development into neural tracts. This matrix can also allow the ingrowth and formation of new blood vessels. If the biological matrix is implanted into the lungs, collagen will be synthesized as well as elastic fibers to provide the necessary basement membrane structure for epithelial cell attachment as well as the elastic expansion capabilities of the lung. The unique matrix structure can synthesize essential proteoglycan matrix materials if implanted into cartilage. Implantation of the matrix into a hyperglycemic pancreas will induce the matrix to form insulin-producing islet cells.

This biological scaffolding material can be derived from one tissue type and placed at another site with therapeutic effect. For instance, blood derived scaffolding material can be used to repair spinal cord defects. In addition, the natural biological matrix generated in vitro can survive various manufacturing and processing procedures such as freezing, heating, and reshaping to optimize desired characteristics. Additionally, these procedures are consistent with good manufacturing practices and will help ensure qualities such as being free of microbial contamination. Additives, such as hydrogels and adhesives, can contribute desired properties to the scaffolding (such as shape, stability, and strength).

The conditions amenable to treatment are also many and varied. For example, implantation of the matrix or scaffolding material into the heart will induce the scaffold to generate heart muscle, while implantation into the pancreas, will induce the scaffold to generate insulin-producing islets. A scaffold that produces insulin can be used to treat diabetes. Matrix production has been observed in in vitro cultures from cells isolated from many different organ systems. The cells in the matrices observed so far are capable of doubling in less than about 24 hours. As such, they are capable of, and have been observed to produce approximately one cubic centimeter of matrix material with enmeshed cells for every cc of blood drawn within a two and a half week period.

The in vitro production of the natural biological matrix is plentiful and the matrix is adaptable in terms of sourcing as well as implantation. The dynamic matrix evolves in a manner appropriate to where it is implanted. Additionally, the enmeshed cells (many of which are pluripotent) add versatility. The natural matrix scaffolding is responsive to external micro-environmental tissue cues, and this responsiveness can provide the essential type of matrix structure and environment conducive to the precise matrix guidance of tissue construction. For example, the pattern of collagen, basement membrane, reticular fibers, or laminin can be synthesized by the spore-like cells. These structures provide guidance for the organization of tissue including the attachment of tissue to the matrix. The synthesis of these guidance structures can occur in concert with the synthesis of other essential structures, such as basement membrane. The synthesis of basement membrane provides for epithelial attachment and interaction with mesenchymal connective tissue, and also allows for the ingrowth of blood vessels. The natural matrix lends itself well to processing and manufacturing methods commonly used for biological materials, such as freezing and heating, as well as reshaping procedures, such as weaving. Certain processes, including freezing and heating can also help ensure sterility of the matrix product.

Figure 1:
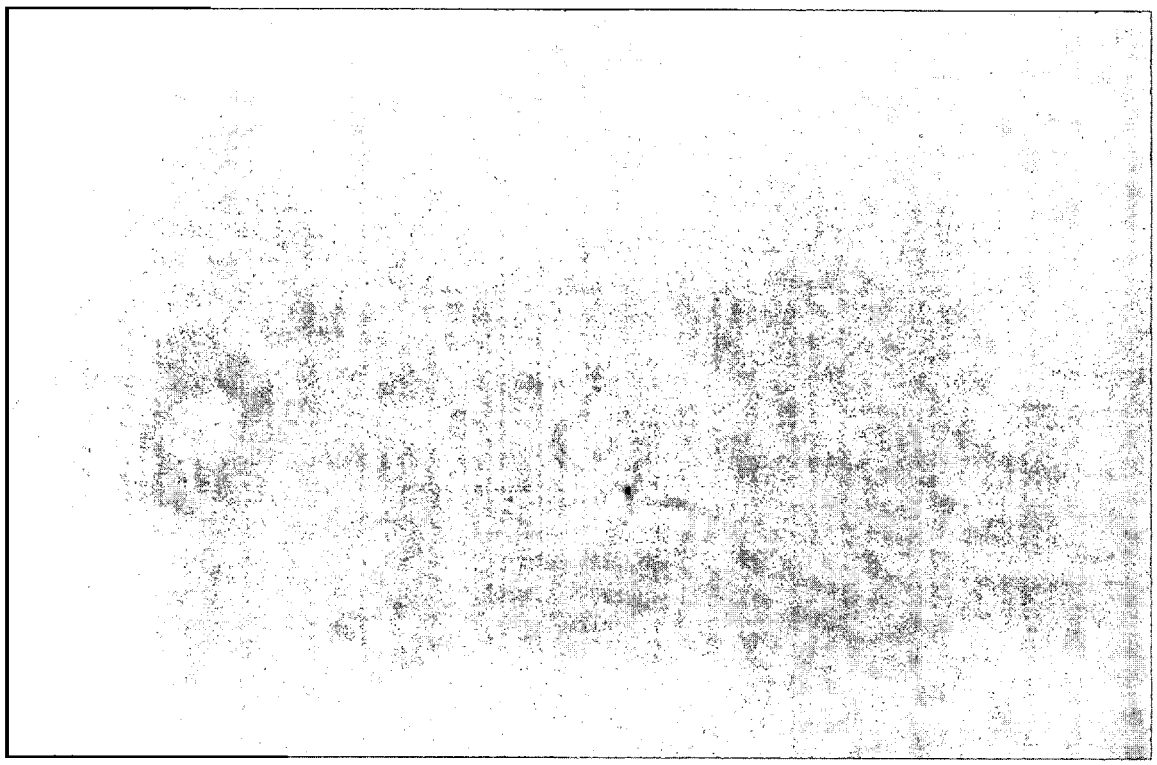
FIG. 1 is a photomicrograph of floating spore-like cells (400×) from the bone marrow of a wooly mammoth (estimated to be about 30,000 years old). The cells form a cellular matrix.

The natural biological scaffolding of the invention can be generated from a variety of sources, including bodily fluids, such as blood or cerebrospinal fluid, or an organ tissue of the body, such as heart or pancreas. As detailed in examples below, the scaffolding can be generated from the blood of a subject (e.g., a human and a rat) and from auricular cartilage from a human. Furthermore, the matrix has also been generated from rat salivary gland and from the scapula of a 30,000 year old wooly mammoth (FIG. 1). Thus, the matrix can be formed from tissue derived from a living or a deceased subject.

To obtain the cells and the materials necessary to generate a new biological scaffolding, a piece of tissue from a donor can be placed in a buffered solution (e.g., phosphate buffered saline), which can include one or more antibiotics, and the tissue can be dissociated mechanically (e.g., by macerating the tissue or by scraping it with a scalpel or similar instrument; the flat blade of a #11 scalpel is particularly effective), chemically (e.g., by exposure to one or more enzymes, such as trypsin or collagenase, that facilitate tissue degradation), or both. Generally, the more aggressive the dissociation, the fewer fully differentiated cells one will obtain. While spore-like cells can be isolated from larger, more differentiated cells by a procedure that includes trituration with a pipette having a reduced bore, one of ordinary skill in the art will recognize that trituration is not the only way to isolate spore-like cells from larger, more differentiated cells.

For example, a suspension containing spore-like cells and fully differentiated cells can be passed through a filter having pores of a particular size. The size of the pores within the filter (and, similarly, the diameter of the pipette used for trituration) can be varied, depending on how stringent one wishes the isolation procedure to be. Generally, the smaller the pores within the filter, or the smaller the diameter of the pipette used for trituration, the fewer the number of differentiated cells that will survive the isolation procedure.

A very practical source of the natural biological matrix is blood, which provides an essentially unlimited amount of autologous, allogenic natural scaffolding material, because clinically it is possible to remove 500 cc of blood from an individual weekly. The blood would also be an unlimited source of xenogenic material. By one particular method described in the examples below (see Example 5), the blood (for example, a sample of blood from a human) is first frozen to at least about $-70°$ C.; the blood can be stored in this state for many weeks or months. The blood can be frozen to at least about $-90°$ C., $-85°$ C., $-80°$ C., $-75$ or $-70°$ C. To generate the biological matrix, the blood is thawed, resuspended in nutrient medium, and then triturated to disperse the cells (including, spore-like cells) and cellular remnants. Most large differentiated cells do not survive the freeze-thaw process. The triturated mixture is filtered, for example, through a mesh having a pore size of about 100 µm to isolate the cells together with an amount of cellular building blocks including, but not limited to, lipids and polysaccharides. The tissue can be filtered through mesh with a pore size of, for example, about 30, 50, 70, 90, 110, 130, 150, 200, 300, 400, or 500 µm. The resulting filtrate is resuspended in culture medium, such as 15× neural culture medium, and then incubated in a tissue culture incubator. The cultured mixture is then separated or extracted from the culture medium, e.g., by centrifugation or filtration, to form the living biological matrix.

The addition of specific nutrients or growth factors will encourage the differentiation of particular cell types. For example, addition of sugar to the culture media facilitates the growth of islet cells in the matrix. In another example, the development of chondrocytes requires treatment with additional growth factors. Incubation can occur, for example, at about $37°$ C. with about 5% $CO_2$. Culturing in these conditions will cause the formation of the matrix.

Trituration is carried out by passing the sample of blood or a tissue sample through a series of devices (e.g., size-exclusion devices such as pipettes or filters) having progressively smaller apertures (the smallest of which can be approximately 15 µm). The process of trituration breaks apart large differentiated cells, but allows the smaller cells including, but not limited to, spore-like cells, to survive. Trituration also necessarily disperses the cells. While these smaller cells, including the spore-like cells, can be isolated from larger, more differentiated cells by a procedure that includes trituration with a pipette having a reduced bore, one of ordinary skill in the art will recognize that trituration is not the only way to isolate the smaller cells from larger, more differentiated cells.

In another aspect of the invention, the cellular matrix can be generated from a sample of auricular cartilage from a subject, such as a human patient. By this particular method, described in detail in Example 1 below, the perichondrium is removed under sterile conditions and the cartilage is fragmented into small pieces, for example, by manual disruption with a scalpel (e.g., a #11 scalpel) and/or a Pasteur pipette. The tissue can also be digested chemically, e.g., with collagenase II, for at least 8 hours, preferably from about 8-12 hours. The mixture is then washed in solution containing antibiotics, e.g., penicillin, streptomycin, and/or amphotercin B, and then the resulting cell suspension is passed through a mesh filter having a pore size of about 250 mm. The pore size can be about 150, 200, 250 or 300 mm. The filtrate is centrifuged and then the cell pellet containing cells (e.g., spore-like cells), chondrocytes, and cell debris is washed and plated in culture media.

The final cell suspension contains small cells and chondrocytes as well as associated extracellular material. The isolated cell mixtures can be cultured in a medium such as Ham F12 culture medium, which can be supplemented with a mixture including, for example, L-glutamine, L-ascorbic acid, penicillin, streptomycin, and amphotercin B, supplemented with about 10% fetal bovine serum. The cells can be incubated in, for example, 75 $cm^2$ tissue culture flasks, at about 37° C. in about 5% $CO_2$. The medium can be changed approximately every three days. To expand the culture for the generation of larger amounts of matrix material, every time the medium is changed, the decanted medium can be collected and centrifuged. The pellet can then be mixed with fresh medium and suspended in a new tissue culture flask. The culture conditions can be altered to either allow the cells to proliferate and differentiate into specialized cell types or to discourage differentiation. The final matrix is formed by extracting the cell and cell debris mixture from the culture medium.

The invention also provides cells that "seed" the natural biological scaffolding. These cells can be autologous, and they can originate from the blood of a subject or an organ of the body. These cells can produce a scaffold resembling collagen, basement membrane, or laminin. The cells used in the methods described herein can be obtained directly from a donor. For example, mammalian cells (e.g., spore-like cells) and their progeny can be isolated from a rodent, rabbit, cow, pig, horse, goat, sheep, dog, cat, non-human primate, or, preferably, a human. Cells and associated extracellular material can be obtained from a post-natal animal even after it has reached adulthood, and that animal can be the same as the animal subsequently treated with those cells, another animal, or an animal of a different species. In other words, autologous, allogeneic, and xenogeneic cells can be obtained and used to treat a human or another animal. If there is an immune response as a result of such allogeneic or xenogeneic transplants, the patient (the recipient of the cells) can be treated with standard immunosuppressant therapy (e.g., with cyclosporine and/or steroid hormones).

Without limiting the invention to spore-like cells that differentiate by a particular mechanism, it is believed that the rate and direction of differentiation (i.e., the fate of spore-like cells and the associated scaffolding) can be influenced by altering the number and type of differentiated cells to which they are exposed. For example, the more differentiated chondrocytes that remain in a matrix of spore-like cells, the more quickly these undifferentiated cells will differentiate and the more likely it is that they will differentiate into cartilage.

Spore-like cells of the cellular matrix can also differentiate when they establish contact with a tissue within a patient's body or when they are sufficiently close to a tissue to be influenced by substances (e.g., growth factors, enzymes, or hormones) released from the tissue. In other words, a spore-like cell of the matrix can establish contact with a tissue, such as heart muscle or cartilage, by virtue of receiving signals from the tissue. Such signaling would occur, for example, when a receptor on the surface of a spore-like cell, or on the surface of a cell descended from a spore-like cell, such as an immature chondrocyte, binds and transduces a signal from a molecule such as a growth factor, enzyme, or hormone that was released by a tissue within the patient. These agents guide differentiation so that the spore-like cells come to express some and possibly most (if not all) of the same proteins normally expressed by differentiated cells in the tissue in which they have been placed.

Alternatively, or in addition, spore-like cells of the matrix can be induced to differentiate by adding a substance (e.g., a growth factor, enzyme, hormone, or other signaling molecule) to the cell's environment. For example, a substance can be added to the natural biological scaffolding of the invention.

In contrast, exposure to growth factors that stimulate progenitor cell mitosis, such as epidermal growth factor (EGF) and basic fibroblast growth factor (bFGF), help maintain spore-like cells in an undifferentiated state.

When a substance that influences the differentiation of the spore-like cells of a natural biological scaffolding is administered, either systemically or locally, it can be administered according to pharmaceutically accepted methods. For example, proteins, polypeptides, or oligonucleotides can be administered in a physiologically compatible buffer, with or without a carrier or excipient. Of course, either the cells within a patient's body or the cells being administered (here, spore-like cells of the cellular matrix) can be made to express particular factors following genetic manipulation. Thus, spore-like cells or their progeny can differentiate either in culture or in a patient's body, and can do so following contact with a solid support or exposure to substances that are either naturally expressed, exogenously administered, or expressed as a result of genetic manipulation.

Regardless of the stimulus for differentiation, the spore-like cells and associated matrix that will differentiate or have differentiated sufficiently to aid in the maintenance or repair of a tissue, can be administered to a patient, such as to a site of tissue loss due to trauma or disease. Exemplary methods of administration are described below.

While spore-like cells and associated cellular matrix can eventually become fully differentiated, and while this is desirable in some circumstances (e.g., where the cells are used to recreate a histologically mature and complete tissue), not all of the cells administered need to be fully differentiated to achieve successful treatment; spore-like cells of the cellular matrix need only differentiate to a point sufficient to treat the patient. That point can be reached either before or after the matrix is administered to the patient.

Terminal differentiation occurs when a cell of the matrix expresses essentially the same phenotype as a mature cell at the site of implantation. For example, for the purpose of defining this invention, a spore-like cell of a cellular matrix, having been implanted into the pancreas, is differentiated when it expresses essentially the same proteins expressed by the pancreas, e.g., a pancreatic islet cell. Antibodies to these markers are commercially available or otherwise readily attainable.

Terminally differentiated cells can also be identified by their gross morphology, by features that are apparent with electron microscopy, and by the connections they form with other cells. For example, cells that differentiate into pancreatic cells can form large clusters that resemble islets and produce insulin; cells that differentiate into liver can obtain hepatocyte morphology and contain bile; lung cells can develop complex morphology resembling bronchioles.

The invention also provides for methods of treating a patient by implanting the natural biological scaffolding into a tissue of the patient, such as the heart, pancreas, lung, spinal cord, or cartilage. After implantation, the matrix can respond to environmental cues that will cause it to develop characteristics of the endogenous tissue. For example, if the matrix is implanted into cartilage, it will be induced to produce proteoglycans. However, if the matrix is implanted into lung tissue, it will be induced to synthesize a collagen and/or an elastic fiber. The matrix can also be implanted into tissues of the central nervous system, where it will be induced to synthesize laminin. Laminins will allow neurons in the tissue to attach to the matrix and guide their development, e.g., into neural tracts. The matrix can also be implanted into the heart, where it will synthesize heart muscle, or into the pancreas, where it will synthesize islet cells. Thus, the implanted matrix will develop characteristics that liken it to the surrounding tissue. By these methods, the biological scaffolding can augment the tissue; the biological scaffolding of the invention can be used for tissue engineering and in any conventional tissue engineering setting.

The new biological matrix can be administered directly, without any support structures. For example, the matrix can be suspended in a physiologically compatible solution and injected into an organ or tissue. For example, the matrix can be applied directly by syringe and needle or micro-catheter to an area of tissue that has been damaged or adversely affected by disease. Development of the spore-like cells enmeshed in the injected matrix will be driven by factors in the local environment and will replenish and repopulate the area.

The natural biological matrix described herein can be used to form a scaffold by adding hydrogels or other materials that provide added shape, structure, or support. A variety of hydrogels can be used to prepare the new biological scaffolds. They include, but are not limited to: (1) temperature-dependent hydrogels that solidify or set at body temperature, e.g., PLURONICS™; (2) hydrogels cross-linked by ions, for example, sodium alginate; (3) hydrogels set by exposure to either visible or ultraviolet light, for example, polyethylene glycol polylactic acid copolymers with acrylate end groups; and (4) hydrogels that are set or solidified upon a change in pH, for example, TETRONICS™. Examples of these types of hydrogels for use in tissue engineering are known in the art.

The materials that can be used to form these various hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Once a hydrogel of choice (e.g., a thermosensitive polymer at between about 5 and 25% (w/v), or an ionic hydrogel such as alginate dissolved in an aqueous solution (e.g., a 0.1 M potassium phosphate solution, at physiological pH, to a concentration between about 0.5% to 2% by weight) is prepared, the biological matrix can be suspended in the polymer solution. The concentration of the cells can mimic that of the tissue to be generated. For example, the concentration of cells can range from between about 10 and 100 million cells/ml (e.g., between about 20 and 50 million cells/ml). Of course, the optimal concentration of cells to be delivered into the support structure can be determined on a case by case basis, and may vary depending on cell type and the region where the support structure is implanted or applied. To optimize the procedure (i.e., to provide optimal viscosity and cell number), one need only vary the amount of matrix or hydrogel.

An adhesive can be used to augment the natural biological matrix. For example, the presence of a hydrogel will often detract from the adhesive strength of a scaffolding. A hydrogel necessarily has a high water content, and the water in the gel cannot and will not adhere to, for example, bone or cartilage. A hydrogel can augment the biological scaffolding, for example, to make the final material more slippery, rather than sticky. In addition, hydrogels that are selected for toughness, smoothness, and durability, but also to provide a non-rigid, non-brittle cushioning, such as in a manner similar to cartilage, may not also have characteristics of an ideal adhesive.

Adhesive polymers can be used to provide additional substrate for cell movement, thereby promoting cell growth and allowing retention of differentiated cell function. These polymers possess physical characteristics that can allow for large surface to volume ratios, contribute to mechanical strength, and be easily processed into complex shapes, such as for bone substitutes. An adhesive supplement should be rigid enough to help the natural scaffold maintain a desired shape in vivo.

An adhesive can be a hot-melt or solvent-based product. An adhesive polymer can be chosen to customize the desired melting point of the hot-melt and its changes in morphology during tackifying and hardening. Adhesive polymers for use in tissue engineering are known in the art.

A support structure is a permeable structure having pore-like cavities or interstices that shape and support the hydrogel-matrix mixture. For example, a support structure can be a porous polymer mesh, or a natural or synthetic sponge. Preferably, the support structure will be biodegradable and transparent. The porosity of the support structure should be such that nutrients can diffuse into the structure, thereby effectively reaching the cells inside, and waste products produced by the cells can diffuse out of the structure.

A support structure can be shaped to conform to the space in which new tissue is desired. For example, a support structure can be shaped to conform to the shape of an area of a pancreas that has been damaged. Depending on the material from which it is made, the support structure can be shaped by cutting, molding, casting, or any other method that produces a desired shape. Moreover, the shaping process can occur either before or after the support structure is filled with the natural biological matrix.

The support structure is also biocompatible (i.e., it is not toxic to the cells suspended therein) and can be biodegradable. For example, the support structure can be formed from a synthetic polymer such as a polyanhydride, polyorthoester, or polyglycolic acid. The polymer should provide the support structure with an adequate shape and promote cell growth and proliferation by allowing nutrients to reach the cells by diffusion. Additional factors, such as growth factors, other factors that induce differentiation or dedifferentiation, secretion products, immunomodulators, anti-inflammatory agents, regression factors, biologically active compounds that promote innervation or enhance the lymphatic network, and drugs, can be incorporated into the polymer support structure. An example of a suitable polymer is polyglactin, which is a 90:10 copolymer of glycolide and lactide, and is manufactured as VICRYL™ braided absorbable suture (Ethicon Co., Somerville, N.J.). Polymer fibers, such as VICRYL™, can be woven or compressed into a felt-like polymer sheet, which can then be cut into any desired shape.

Alternatively, the polymer fibers can be compressed together in a mold that casts them into the shape desired for the support structure. In some cases, additional polymer can be added to the polymer fibers as they are molded to revise or impart additional structure to the fiber mesh. For example, a polylactic acid solution can be added to this sheet of polyglycolic fiber mesh, and the combination can be molded together to form a porous support structure. The polylactic acid can bind the crosslinks of the polyglycolic acid fibers, thereby coating these individual fibers and helping to fix the shape of the molded fibers. The polylactic acid can also fill in spaces between the fibers. Thus, porosity can be varied according to the amount of polylactic acid introduced into the support. The pressure required to mold the fiber mesh into a desirable shape can be quite moderate. All that may be required is that the fibers be held in place long enough for the binding and coating action of polylactic acid to take effect.

Alternatively, or in addition, the support structure can include other types of polymer fibers or polymer structures produced by techniques known in the art. For example, thin polymer films can be obtained by evaporating solvent from a polymer solution. These films can be cast into a desired shaped if the polymer solution is evaporated into a mold having the relief pattern of the desired shape. Polymer gels can also be molded into thin, permeable polymer structures using compression molding techniques known in the art.

Many other types of support structures are also possible. For example, the support structure can be formed from a sponge, foam, or biocompatible inorganic structure having internal pores, or from mesh sheets of interwoven polymer fibers. These support structures can be prepared using known methods.

Any of the natural scaffolding or liquid hydrogel-matrix mixtures described herein can be placed into any permeable support structure (also described herein). The scaffolding or liquid hydrogel-matrix mixture can be delivered to the shaped support structure either before or after the support structure is implanted into a patient. The specific method of delivery will depend on whether the support structure is sufficiently "sponge-like" for the given viscosity of the scaffolding or hydrogel-matrix composition, i.e., whether the support structure easily retains the biological scaffolding or liquid hydrogel-matrix mixture before it solidifies. Sponge-like support structures can be immersed within, and saturated with, the biological scaffolding or liquid hydrogel-matrix mixture, and subsequently removed from the mixture. The biological scaffolding or hydrogel is then allowed to solidify within the support structure. The biological scaffold- or hydrogel-matrix-containing support structure can then be implanted in or otherwise applied to the patient.

The support structure can also be applied to the patient before the hydrogel completely solidifies. Alternatively, a sponge-like support structure can be injected with the biological scaffolding or liquid hydrogel-matrix mixture, either before or after the support structure is implanted. The biological scaffolding or hydrogel-matrix mixture can then be allowed to solidify.

The volume of the biological scaffolding or liquid hydrogel-matrix mixture injected into the support structure is typically less than, but somewhat comparable to the volume of the support structure (i.e., the volume of the desired tissue to be grown).

Support structures that do not easily retain the liquid composition can require somewhat different methods. In those cases, for example, the support structure can be immersed within and saturated with the liquid hydrogel-matrix mixture, which can then be allowed to partially solidify. Once the matrix-containing hydrogel has solidified to the point where the support structure can retain the hydrogel, the support structure can be removed from the partially solidified hydrogel, and, if necessary any partially solidified hydrogel that remains attached to the outside of the support structure can be removed, such as by scraping off the structure.

Alternatively, the liquid hydrogel-matrix mixture can be delivered into a mold containing the support structure. For example, the liquid hydrogel-matrix mixture can be injected into an otherwise fluid-tight mold that contains the support structure and matches its outer shape and size. The hydrogel can then be solidified within the mold, for example, by heating, cooling, light-exposure, or pH adjustment, after which, the hydrogel-matrix-containing support structure can be removed from the mold in a form that is ready for implantation.

In another embodiment, the support structure can be implanted in or applied to the patient (e.g., placed over a damaged or dysfunctional portion of tissue), and the biological scaffolding or liquid hydrogel-matrix mixture can then be delivered to the support structure. The biological scaffolding or hydrogel-matrix mixture can be delivered to the support using any simple device, such as a syringe or catheter, or merely by brushing or spraying a liquid gel onto a sheet-like support structure.

Here again, the volume of biological scaffolding or hydrogel-matrix composition added to the support structure should approximate the size of the support structure (i.e., the volume displaced by the desired tissue to be grown). The support structure provides space and a structural template for the injected biological scaffolding or liquid hydrogel-matrix mixture. As described above, some of the biological scaffolding or hydrogel-matrix mixture may leak from the support structure prior to solidifying. However, in this event, existing tissue would sufficiently constrain the biological scaffolding or liquid hydrogel-matrix mixture until it sets. In addition, body temperature will keep a PLURONICS-based hydrogel-matrix structure in gel form.

In any of the above cases, a hydrogel is solidified using a method that corresponds to the particular hydrogel used (e.g., gently heating a composition including a PLURONIC™ temperature-sensitive hydrogel).

To apply or implant the support structure, the implantation site within the mammalian patient can be prepared (e.g., surgically accessed), and the support structure can be implanted or otherwise applied directly at that site.

The cells that generate the biological matrix can first be expanded to a number that will provide enough natural scaffolding for its desired purpose. For example, cells obtained from a punch biopsy can be cultured and expanded to generate enough cells to create a cellular matrix sufficient to generate a human ear.

The invention is further illustrated by the following examples, which should not be construed as further limiting.

EXAMPLES

Example 1

Expansion of the Number of Human Auricular Chondrocytes: Recycling of Culture Media Containing Floating Cells We have found that cell replication can be enhanced in culture by recycling some of the used cell medium that would otherwise be discarded. Traditionally, for optimal nutrition of chondrocytes, the culture media is changed twice a week, with floating media being replaced by fresh media. Floating media (or supernatant), which contains some floating non-specific and presumably useless debris, is normally discarded. However, when this same floating medium was placed in a new culture flask, chondrocytes grew in monolayer cultures. This observation led to a practice of supernatant recycling and to culture methods that produced an increase in the yield of auricular chondrocytes.

The aim of the present study was to investigate and quantify the ability of in vitro chondrocytes multiplied by this recycled supernatant technique to generate neo-cartilage in vivo. Flow cytometry was used to differentiate the floating structures and to identify the source of the chondrocytes generated from the decanted media.

A three mm biopsy of human pediatric auricular cartilage was obtained from otological procedures. The perichondrium was removed under sterile conditions and the cartilage was fragmented into small pieces, washed in phosphate-buffered saline (PBS) solution containing 100 u/L of penicillin, 100 mg/L of streptomycin and 0.25 mg/L of amphotercin B (Gibco, Grand Island, N.Y.), and then digested with 0.3% collagenase II (Worthington Biochemical Corp., Freehold, N.J., USA) for 8-12 hours. The resulting cell suspension was passed through a sterile 250 mm mesh filter (Spectra/Mesh 146-426; Spectrum Medical Industries, Inc., Laguna Hills, Calif.). The filtrate was centrifuged and the resulting cell pellet was washed twice with copious amounts of Dulbecco's PBS. Cell number and viability was determined by cell count using a hemocytometer and trypan blue dye. The chondrocyte suspensions demonstrated cell viability in excess of 85%.

In Vitro Cultures

Chondrocytes were plated in 75 $cm^2$ culture flasks (Falcon, Becton Dickinson, N.J., USA). These chondrocytes were suspended in Ham F12 culture medium (Life Technologies, Baltimore, Md.) with L-glutamine, 50 mg/L L-ascorbic acid, 100 u/L of penicillin, 100 mg/L of streptomycin, 0.25 mg/L of amphoterecin B, supplemented with 10% fetal bovine serum (Sigma-Aldrich, St, Louis, Mo., USA). The cell cultures were maintained in monolayers at 37° C. and 5% $CO_2$, and the culture media was changed twice a week. Every time the medium was changed, the decanted media was collected and centrifuged. The pellet was mixed with fresh media and suspended in a new 75 $cm^2$ flask. In this way, multiple 75 $cm^2$ culture flasks were created from the decanted media, which would usually have been discarded. Original chondrocytes were serially trypsinized at 80% confluence with 0.25% Trypsin/EDTA (Sigma-Aldrich, St Louis, Mo., USA) and as their number increased with time and passaging, so did the number of cells from the decanted media.

Two groups of cells, Group A (fresh; attached) and Group B (decanted; floating) were created. Cells from both the groups were trypsinized at 80% confluence with 0.25% Trypsin/EDTA. Cell number and viability were determined by cell count using a hemocytometer and trypan blue dye. A concentration of about 30-40 million cells was used in 1 ml of polymer for in vivo implantation to generate cartilage.

For cells grown in monolayer culture, cell numbers increased proportionally with the number of passages. The initial population of Group A cells in each of the four subgroups expanded to about 100-130 million cells after the second passage. The cell population from the decanted media also grew in proportion to the original chondrocytes. At the end of the second passage, the average concentration in each of the four subgroups of Group B (floating cells) was about 30-40 million cells/subgroup. This extra 30% increase from the decanted media in the number of chondrocytes appeared to be due to the floating cells.

In Vivo Studies

All the cells used for in vivo implants were suspended in a hydrogel, Pluronic F 127, a co-polymer formed with 70% polyethylene oxide and 30% of polypropylene oxide (BASF, Mount Olive, N.J.) at 4° C. at a concentration of 30-40 million chondrocytes/ml. A total of 6 athymic mice, at 4 weeks of age, were injected in the dorsal subdermal space under general anesthesia. A mixture of chondrocytes from Group B (floating cells) and Pluronic 127 was injected into four mice. Two control mice received the mixture of Pluronic F 127 and Group A chondrocytes (original cells). Specimens were harvested after eight weeks from mice that were killed from an overdose of anesthetic. The constructs were removed aseptically and were fixed in 10% phosphate-buffered formalin (Fisher Scientific, Fair Lawn, N.J.) for histological analysis.

Histological Analysis

Once fixed for at least 24 hours, specimens were embedded in paraffin and sectioned using standard histochemical techniques. Slide sections were stained with hematoxylin & eosin (H&E) and Safranin O.

Histology slides from the Group A cells (FIG. 2) revealed fragments of lobular cartilaginous tissue. The lacunae were round to oval, and in many cases did not form discreet boundaries. The lacunae did contain single cells with rounded nuclei. The specimen was highly cellular and somewhat irregular in architecture. There were some cellular areas of fibrous tissue with a sprinkling of chronic inflammation. The matrix was lightly basophilic in the cartilaginous areas and eosinophilic in the more fibrous areas. Additional sections displayed more discreet cartilage formation with more regularly spaced and shaped lacunae containing single cells. The histology slides from the Group B cells (FIG. 3) revealed fragments of myxoid tissue with a lightly eosinophilic matrix with focal areas of more evenly spaced cells and a hint of lacunae formations suggestive of immature cartilage. Additional sections essentially showed the same histology but more discreet areas of immature cartilage formation of a myxoid quality with a hint of lacunae formation and a very slight basophilic tint in the center of the immature cartilage regions. Safranin O (on the same sections) revealed positivity centrally in the immature cartilaginous areas consistent with proteoglycan production.

Flow Cytometric Studies

Cells were collected from both the floating media and the attached monolayer cell culture. The medium containing the floating cells was centrifuged to harvest the cells, and the attached cells were collected after treatment with 0.05% trypsin. The cells from both groups were fixed in 90% ethanol. After overnight fixation at 4° C., cells were incubated at 37° C. for 20 minutes in PBS containing 50 µg/ml of RNAase and 20 µg/ml propidium iodide (Crissman et al., Cytometry 3: 84-90, 1982). Flow cytometry was performed on a FACScan equipped with pulse processing electronics (BD Biosciences, San Jose, Calif.). Minimums of 15,000 cells were analyzed.

Two distinct populations were observed by this method. FIG. 4 is a scattergram of the attached cell population showing side scatter (Y-axis) versus forward scatter (X-axis). A distinct population of intermediate forward scatter and low to moderate side scatter reflecting a medium sized cell with low granularity, which is characteristic of chondrocytes, was demonstrated. There was also evidence of apoptotic bodies as seen in the areas proximal to the intersection of the X and Y-axis.

FIG. 5 is a scattergram of the floating cell population. This population was comprised predominantly of a distinct population with moderate to high side scatter and low forward scatter indicating a small cell with granular characteristics. A small percentage of cells overlapped in the coordinates found with chondrocytes. Thus, the scattergram indicates two distinct populations of floating cells.

Generally, about 10 mgs of cartilage taken from a biopsy can provide an average of about 200 to 250,000 chondrocytes. Approximately 250 million chondrocytes are sufficient to reengineer a tissue the size of an ear. The chondrocytes can be passaged repeatedly and treated with growth factors to improve yield. Using the method applied in this study, after two passages, the average yield from the initial cell number expanded to approximately 130 million. An additional 30-40 million cells was harvested by using the decanted media and these cells also resulted in the formation of cartilage when implanted in vivo. Even after the original cells were implanted, the repeated decanting process continued to provide further multiplication and in vitro growth. Cells obtained in this way could be used for future implantation in the same patient from which they were initially harvested. The initial small number of chondrocytes (300, 000) was successfully expanded to about 200 million in six weeks using the same technique.

The small floating cells in the decanted media appeared by phase microscopy to be very similar to the spore-like cells previously described (Vacanti et al., *J. Cell Biochem.* 80:455-460, 2001). Flow cytometry, successfully used in previous studies of chondrocytes (Kamil et al., *Tissue Engineering* 7:81-88, 2002; Kreicbergs et al., *Cancer* 50:577-583; Alho et al., *J. Bone Joint Surg. Am.* 65: 779-85), and the microscopic examination performed on the decanted media showed the majority of the floating structures to be much smaller than normal adult chondrocytes. Both normal sized mature chondrocytes and smaller floating structures were detected in the media after staining the cells with potassium iodide before performing the flow cytometric studies. Debris and dead cells (also present in the decanted media) stained, but both smaller structures and larger cells did not take up the potassium iodide, identifying two populations of viable cells.

The tissue generated from Group B (floating) cells was more characteristic of embryonic or immature cartilage than Group A cells even though both were harvested after 8 weeks of implantation. The continuous growth of the cells in vitro can be useful clinically to enhance the number of chondrocytes available from a small specimen before implantation. The biological matrix is the mixture of cells and cellular debris extracted, e.g., by centrifugation or filtration, from either or both Groups A and B.

Example 2

Spinal Cord Repair Using Frozen Blood-Derived Biological Matrix

Lewis rat blood was frozen at −20° C. for several weeks, then thawed and added to 15 cc of DMEM/F12 with epidermal growth factor (EGF), b-FGF, and progesterone. The sample was triturated using a Pasteur pipette and a reduced bore Pasteur pipette and then passed through a 100 μm, and then a 40 μm filter, and incubated in a 175 cm$^2$ Costar flask at 37° C. with 5% $CO_2$ for 14 days. The sample was resuspended in fresh media every three days. At day 14, the contents of the flask including cells and debris were centrifuged at 1500 RPMs for 10 minutes yielding approximately ¼ cm$^3$ of material. This condensed mixture of cells and debris was the living biological matrix.

The biological matrix material was analyzed before implantation into rats. The matrix stained positive for Trichrome stain, indicating the presence of collagen, which is not a normal component of blood. Clumps of PAS positive material indicated the presence of mucopolysaccharides and glycolipids, and weak staining by Safranin O indicated a weak presence of proteoglycans.

Each of two male Lewis rats under general anesthesia had a 4 mm segment of spinal cord removed between T8 and T9, and the natural, living, biological matrix was placed into the gaps with the admixed cells. The opening in the vertebra was covered with fibrin glue and a hydroxymethylcellulose membrane, and the surgical incision was closed with sutures. Immediately after the operation, both animals had complete flaccid paralysis below the level of resection. At the fifth postoperative day, one of the animals slowly moved its right leg on several occasions and quickly moved its tail. Both animals regained a full range of motion in their hind legs, and after two months, one animal was able to take coordinated steps. Two negative control rats and a fibrin glue implant control rat failed to demonstrate any significant neurological recovery.

One rat was sacrificed five weeks after the implantation of the frozen rat blood-derived matrix and cells. The attached construct was about 60% the diameter of normal cord (see FIG. 6 and FIG. 7) (observed grossly). On the perimeter of the cord was fibrous scar and callous tissue (FIG. 6; observed grossly). Plump neurons were surrounded by wavy matter. Capillary formation was abundant.

Histology results (not shown) revealed a high concentration of nerve cell bodies admixed with white matter. Peripheral to these were more predominant white matter and membrane-type tissue. These results indicated the implant's attempt to develop spinal cord-encasing membranes such as pia, arachnoid, and dura. On the extreme periphery was observed hard tissue, some of which appeared to be freshly synthesized bone and/or cartilage. The development of these particular tissue types was attributed to the responsiveness of the matrix to the adjacent endogenous tissues at the site of implantation, including gray matter (neurons), white matter, and peripheral nerve tissue that stained positive with Luxol fast blue. The peripheral nerve tissue contained only a scant amount of myelin, indicating that this was new tissue, and not adult tissue. Membranes, bone, and cartilage were also observed at the site of implantation. The cartilage stained positive for Safranin O, and the staining was more intense at and around the point of contact with native cartilaginous disc tissue at the implant site. This staining pattern indicated that the cartilage tissue was immature freshly synthesized cartilage. Histology of tissue from the negative control rats revealed only bony callous and scar tissue. Histology of tissue from the resection site of the fibrin glue implant control revealed only an organized blood clot.

Example 3

Islet-like Structures Generated from Human Blood

Human blood was collected from a patient and anti-coagulated by treatment with heparin. The sample was frozen to −85° C. The blood was then thawed, resuspended in nutrient medium, and triturated to disrupt large differentiated cells and to dissociate spore-like cells and cellular debris. The mixture was filtered through a mesh having a 100 μm pore size to isolate the cells together with an amount of cellular building blocks (or cellular fragments or components) including, but not limited to, lipids and polysaccharides. The filtrate (living biological matrix) was resuspended in nutrient media plus 500 mg % glucose (i.e., 500 mg glucose per cc of blood) and incubated at 37° C. in 5% $CO_2$. The medium was changed every three days.

It is common knowledge that RNA in blood is degraded following a freeze-thaw cycle. After 2 weeks in culture, RNA was extracted from the blood-derived living biological matrix, indicating that the matrix undergoes active protein synthesis. In addition, hematoxylin and eosin (H&E) stain indicated that islet-like structures having clusters of nucleated cells were produced by day 19 in culture. In a biological matrix generated from blood of a juvenile diabetic, C-peptide was detected in the culture media, indicating insulin production and secretion. The observation of endoderm tissue (e.g., islets), mesoderm tissue (e.g., bone, cartilage, membranes, and blood vessels), and ectoderm tissue (e.g., neurons, such as peripheral nerves) in the derived biological matrix indicated that the matrix was pluripotent.

Example 4

Implantation of Blood-Derived Islet Cells Resulted in Decreased Blood Glucose Levels Human blood was collected from a juvenile diabetic who had the disease for eight years. The blood was processed as described in Example 3. Islet-like structures derived from the matrix material were implanted into the peritoneums of two diabetic adult rats. Both rats demonstrated a 5-day drop in blood glucose levels to an average of 80 mg %. Two control animals died. The drop in glucose levels was temporary.

Example 5

A Biological Matrix Generated from Human Blood

Human blood was collected from a patient and processed as described in Example 3. The filtrate was resuspended in nutrient medium and incubated at 37° C. with 5% $CO_2$. The medium was changed every three days. The results are shown in FIGS. 8-13.

Microscopy and histology analyses indicated the formation of cells and matrix material by day 19 of culture incubation (see FIGS. 10 and 12). FIG. 10 is a gross image of floating matrix material, at day 19, prepared from frozen, anticoagulated human blood. FIG. 12 is also an image (at 400× resolution) of matrix material, at day 19, prepared from frozen, anticoagulated human blood. The H&E staining of FIG. 11 provides a contrast that distinguishes the matrix material (darkly stained) from the cellular debris (lightly stained). PAS staining indicated the presence of glycolipids and mucopolysaccharides (FIG. 8), and Safranin O staining indicated the capacity to make proteoglycans, the matrix material found in cartilage (FIG. 9).

Approximately 40% of the developing matrix stained PAS positive, reflecting mucopolysaccharides and glycolipids (FIG. 8). Approximately 20% of the matrix stained trichrome positive indicating the presence of collagen (FIG. 13). Safranin O staining (see FIG. 9) indicated that proteoglycans made up a very small percentage (1%) of the matrix. A large amount of debris, including ruptured red blood cell membranes and uncharacterized material was also evident.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of generating a living biological matrix in vitro, the method consisting essentially of: (a) obtaining a cell sample; (b) disrupting the cell sample to create a mixture containing cells and cellular debris; (c) culturing the mixture, retaining the cellular debris, in culture medium for a time and under conditions sufficient to form a living biological matrix in vitro; and (d) separating the biological matrix from the culturing medium, wherein the cells include spore-like cells.

2. The method of claim 1, wherein the cell sample of step (a) is obtained from a subject who will be a recipient of the biological matrix.

3. The method of claim 1, wherein the cell sample of step (a) is obtained from a human.

4. The method of claim 1, wherein the cell sample comprises a bodily fluid.

5. The method of claim 4, wherein the bodily fluid is blood.

6. The method of claim 4, wherein the bodily fluid is cerebrospinal fluid.

7. The method of claim 1, wherein the cell sample comprises a portion of an organ.

8. The method of claim 1, wherein the cell sample comprises aurticular cartilage.

9. The method of claim 8, wherein before disrupting the cell sample, the perichondrium is removed from the cartilage.

10. The method of claim 1, further adding to the separated mixture a component that adds shape, structure, or support to the matrix.

11. The method of claim 10, wherein the component is a hydrogel or an adhesive.

12. The method of claim 1, further adding to the matrix an antibiotic.

13. A method of augmenting a tissue defect in a subject, the method comprising: (a) preparing a living biological matrix according to the method of claim 1; and (b) administering the living biological matrix to the subject in the region of the tissue defect, wherein the matrix develops a characteristic of the endogenous tissue and thereby augments the tissue defect.

14. The method of claim 13, wherein the tissue defect is in a muscle.

15. The method of claim 14, wherein the muscle is the heart.

16. The method of claim 13, wherein the tissue defect is in a portion of a lung, pancreas, spinal cord, joint, head, neck, skin, kidney, or liver of the subject.

17. The method of claim 13, wherein the subject is a human.

18. A living biological matrix comprising cells, cell fragments, lipids, and polysaccharides,
    wherein the matrix is made by a method consisting essentially of (a) obtaining a cell sample;
(b) disrupting the cell sample to create a mixture containing cells and cellular debris;
(c) culturing the mixture, retaining the cellular debris, in culture medium for a time and under conditions sufficient to form a living biological matrix in vitro; and
(d) separating the biological matrix from the culturing medium, wherein the cells include spore-like cells.

19. The matrix of claim 18, further comprising a component that adds shape, structure, or support to the matrix.

20. The matrix of claim 18, further comprising a hydrogel or adhesive.

21. The matrix of claim 18, further comprising an antibiotic.

22. The matrix of claim 18, further comprising a cellular component selected from the group consisting of a fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, and hyaluronic acid.

23. The matrix of claim 18, wherein the cell sample of step (a) is obtained from a subject who will be a recipient of the biological matrix.

24. The matrix of claim 18, wherein the cell sample is obtained from a human.

25. The matrix of claim 18, wherein the cell sample comprises a bodily fluid.

26. The matrix of claim 25, wherein the bodily fluid is blood.

27. The matrix of claim 25, wherein the bodily fluid is cerebrospinal fluid.

28. The matrix of claim 18, wherein the cell sample comprises a part of an organ.

29. The matrix of claim 18, wherein the cell sample comprises auricular cartilage.

30. The matrix of claim 29, wherein, before disrupting the cell sample, the perichondrium is removed from the cartilage.

31. The matrix of claim 18, wherein the biological matrix is added to shape, structure, or support material.

32. A method of augmenting a tissue defect in a subject, the method comprising: (a) obtaining a living biological matrix of claim 18; and (b) administering the living biological matrix to the subject in the region of the tissue defect, wherein the matrix develops a characteristic of the endogenous tissue and thereby augments the tissue defect.

* * * * *

UNITED STATES PATENT AND TRADEMARK OFFICE
CERTIFICATE OF CORRECTION

PATENT NO.        : 7,319,035 B2  
APPLICATION NO.   : 10/688305  
DATED             : January 15, 2008  
INVENTOR(S)       : Martin P. Vacanti and Charles A. Vacanti Page 1 of 1

It is certified that error appears in the above-identified patent and that said Letters Patent is hereby corrected as shown below:

Claim 8, column 20, line 37, replace "auritcular" with --auricular--.

Signed and Sealed this

Twenty-second Day of July, 2008

JON W. DUDAS  
*Director of the United States Patent and Trademark Office*